United States Patent [19]

Shibanai

[11] Patent Number: 4,636,343

[45] Date of Patent: Jan. 13, 1987

[54] PROCESS FOR THE PREPARATION OF INSECT REPELLING/KILLING FILM

[76] Inventor: Ichiro Shibanai, 10-6-312, Akasaka 6-chome, Minato-ku, Tokyo, Japan

[21] Appl. No.: 774,197

[22] Filed: Sep. 9, 1985

[30] Foreign Application Priority Data

Sep. 10, 1984 [JP] Japan ................... 59-188212

[51] Int. Cl.$^4$ ........................................... B29C 59/02
[52] U.S. Cl. ................................... 264/118; 106/15.05; 127/38; 264/12; 264/142; 264/143; 264/175; 264/176.1; 264/210.6; 264/211; 264/515; 424/78; 424/83; 514/58
[58] Field of Search ............... 264/118, 142, 143, 515, 264/564, 210.6; 260/954; 127/38; 514/58; 536/103; 106/15.05; 424/78, 83

[56] References Cited

U.S. PATENT DOCUMENTS

| | | | |
|---|---|---|---|
| 3,091,565 | 5/1963 | Suzuki et al. | 260/954 X |
| 4,136,145 | 1/1979 | Fuchs et al. | 264/210.6 X |
| 4,189,458 | 2/1980 | Jezl | 264/143 |

FOREIGN PATENT DOCUMENTS

| | | | |
|---|---|---|---|
| 0205117 | 12/1982 | Japan | 264/515 |
| 0150577 | 9/1983 | Japan | 514/58 |

Primary Examiner—Donald Czaja
Assistant Examiner—Harold Y. Pyon
Attorney, Agent, or Firm—Jordan and Hamburg

[57] ABSTRACT

A process for the preparation of insect repelling/killing film. The process involves forming a clathrate compound of fenitrothion with cyclodextrin or a starch decomposition product containing cyclodextrin, at the same time granulating said clathrate compound into dry powder, melt-mixing said dry powder with a synthetic material, which is an olefin, soft vinyl chloride, or vinyl acetate plastic, in an amount of 0.1 to 50% (weight ratio), molding said mixture into pellets, and molding said pellets or a mixture of an appropriate amount of said pellets with a synthetic resin material in the form of film.

12 Claims, No Drawings

PROCESS FOR THE PREPARATION OF INSECT REPELLING/KILLING FILM

BACKGROUND OF THE INVENTION

1. Field of the Invention

The present invention relates to a process for the preparation of a synthetic resin film having insect repelling/killing abilities, in which fenitrothion is used as insect repellent/killer.

2. Description of the Prior Art

Films having insect repelling/killing abilities are used for wrapping fruits when they are transported, for wrapping clothes, or as underlay for tatami or carpet, effectively protecting fruits or clothes from insect damage and preventing the growth of mite under tatami or carpet.

Films having insect repelling/killing abilities can be largely classified into two groups, i.e. those prepared by interleaving a lamination of synthetic resin sheets or paper with an insect repellent/killer, and those prepared by applying an insect repellent/killer on synthetic resin sheets or paper, or impregnating them with an insect repellent/killer.

Those prepared by interleaving a lamination with an insect repellent/killer are limited in the reduction of its thickness, so that it cannot be formed into thin film.

On the other hand, those prepared by applying an insecticide on synthetic resin sheets or paper exert an insect repelling/killing effect only in a short period because the insecticide applied on the surface of the substrate is directly exposed to outside. It is difficult to impregnate synthetic resin with an insecticide, although paper can be impregnated. It has not been attempted so far to incorporate an insecticide with a synthetic resin material when the resin is molded and to form it into film.

Under these circumstances, it has been expected to develop a product which can be molded into film, in which an insecticide is incorporated with a synthetic resin material, characterized in that the obtained film shows not only a homogeneous but also prolonged insect repelling/killing effect, in such a manner that the insecticide appropriately bleed to the surface of the film.

SUMMARY OF THE INVENTION

The process for the preparation of insect repelling/killing film according to the present invention is characterized in forming a clathrate compound of fenitrothion with cyclodextrin or a starch decomposition product containing cyclodextrin, at the same time forming said clathrate compound into dry powder, melt-mixing said power with a synthetic resin material in an amount of 0.1 to 50% (weight ratio), molding said mixture into pellets, and molding said pellets or a mixture of an appropriate amount of said pellets with a synthetic resin material in the form of film. Formation of a clathrate compound of fenitrothion, the insect repellent/killer used in the present invention, with cyclodextrin can afford a homogeneous mixture with a synthetic resin material and enables fenitrothion to appropriately bleed to the surface of the film when the mixture of the clathrate compound with the synthetic resin material is molded in the form of film.

DETAILED DESCRIPTION OF PREFERRED EMBODIMENTS

Fenitrothion used in the present invention (Sumithion in brand name; manufactured by Sumitomo Chemical Co., Ltd.) is represented by the chemical name: O,O-dimethyl-O-(3-methyl-4-nitrophenyl)thiophosphate. Fenitrothion is employed as the insect repellent/killer for the present invention because of its excellent effect and safety due to its low toxicity. Also, it can be easily formed into clathrate compound with cyclodextrin and incorporated with a synthetic resin material for molding because of its high resistance to heat.

Cyclodextrin used in the present invention is a special dextrin, in which D-glucose molecules are linked circularly by the α-1,4-bond, and characterized in a doughnut-like molecular structure with a hollow inside, the diameter of said hollow ranging from 6 to 10 Å. There are three types of cyclodextrin, i.e. α-type, β-type, and γ-type, classified according to the number of the structural units of D-glucose. Any of these three types can be used in the present invention. Among them, β-cyclodextrin is in the form of white crystalline powder and represented by the molecular formula of $(C_6H_{10}O_5)_7$. The molecular weight is 1135 and the melting point ranges from 300° to 305° C. (dec.).

Starch decomposition products containing cyclodextrin, which can be used instead of cyclodextrin, can be obtained by various methods, which include, for example, those obtained as the intermediate in the preparation of cyclodextrin by the action on starch of a cyclodextrin-producing enzyme formed by the microorganisms belonging to genus Bacillus. The process for the preparation of such intermediate will be described in more detail below.

A liquid containing starch is formed into homogeneous paste, the pH value of which is adjusted to 10, and cooled. Cyclodextrin glycosyltransferase, which is a fermentation product of a microorganism selected from among genera Bacillus No. 13, Bacillus No. 17-1, Bacillus No. 38-2, Bacillus No. 135, and Bacillus No. 169 is added to the liquid for reaction. Said cyclodextrin glycosyltransferase has its optimum pH value in the alkaline range and a high-temperature stability. After the enzyme is deactivated by heating the reaction liquid, the liquid is again cooled, the pH value being adjusted to 5.0. Commercially available glucamylase is added to the reaction liquid to decompose the unreacted substances.

The reaction liquid is then filtered by an ordinary method, concentrated so that 40% or more of cyclodextrin will be contained therein, and a small amount of cyclodextrin is added to the concentrated liquid as seed. After the liquid is left to stand, the precipitates of cyclodextrin deposit, which will be filtered and dried, yielding β-cyclodextrin. The filtrate serves as the desired starch decomposition product containing cyclodextrin (see Japanese Patent Publication No. 43897/1977).

The above-mentioned microorganism, i.e. genera Bacillus No. 13, Bacillus No. 17-1, Bacillus No. 38-2, Bacillus No. 135, and Bacillus No. 169 are all deposited with the Fermentation Research Institute of the Agency of Industrial Science and Technology as FERM-611, 612, 614, 617 and 618.

The products obtained by re-purifying the above-described filtrate by ion-exchange resin and concentrating are commercially available as malt honey containing cyclodextrin. This malt honey can be used also in the present invention.

The starch decomposition products containing cyclodextrin to be used in the present invention are not limited to those obtained by the method described above. Starch decomposition products obtained by any method can be used so long as they contain α, β, or γ-cyclodextrin or a mixture thereof.

The synthetic resin material to be used in the present invention must have a low melting point, because fenitrothion is decomposed at a temperature of 180° C. or higher, though fenitrothion is said to be resistant to high temperatures. As the molding temperatures of some synthetic resin materials are higher than 180° C., it is necessary to select a synthetic resin material that has a molding temperature lower than the heat-resistant temperature of fenitrothion. Such synthetic resin materials preferable for the present invention include olefin plastics, soft vinyl chloride plastics, and vinyl acetate plastics.

The process for the preparation of insect repelling-/killing film of the present invention will be more readily understood by the following examples.

EXAMPLE 1

85 parts by weight of α-cyclodextrin was added to 15 parts by weight of fenitrothion, and the mixture was blended under stirring for 1 hour while keeping the temperature at 50° C., to prepare a clathrate compound of fenitrothion with cyclodextrin. The obtained clathrate compound was granulated into powder having a particle size of 150 mesh or finer with a vacuum drier at a drying temperature of 60° C. 50 parts by weight of the obtained powder and 50 parts by weight of soft vinyl chloride compound were melt-mixed, and molded into pellets by the cold cut method. A mixture of 10 parts by weight of the obtained pellets with 90 parts by weight of the soft vinyl chloride compound was molded in the form of film by calendering.

EXAMPLE 2

90 parts by weight of β-cyclodextrin was added to 10 parts by weight of fenitrothion and the mixture was blended under stirring for 1 hour while keeping the temperature at 50° C., to prepare a clathrate compound of fenitrothion with cyclodextrin. The obtained clathrate compound was granulated into powder of 150 mesh or finer with a spray drier at a drying temperature of 60° C. 30 parts by weight of the obtained powder and 70 parts by weight of soft vinyl chloride compound were melt-mixed, and molded into pellets by the hot cut method. A mixture of 20 parts by weight of the obtained pellets with 80 parts by weight of polyethylene compound was molded in the form of film by extrusion molding.

EXAMPLE 3

85 parts by weight of a starch decomposition product (containing 50% of α,β, and γ-cyclodextrin) was added to 15 parts by weight of fenitrothion, and the mixture was blended under stirring for 1 hour while keeping the temperature at 50° C., to prepare a clathrate compound of fenitrothion with cyclodextrin. The obtained clathrate compound was granulated into powder of 150 mesh or finer with a vacuum drier at a drying temperature of 60° C. 20 parts by weight of the obtained powder and 80 parts by weight of polyethylene pellets were melt-mixed, molded into pellets by the cold cut method, and further molded in the form of film by calendering.

EXAMPLE 4

85 parts by weight of a starch decomposition product (containing 15% of α, β, and γ-cyclodextrin) was added to 15 parts by weight of fenitrothion, and the mixture was blended under stirring for 1 hour while keeping the temperature at 50° C., to prepare a clathrate compound of fenitrothion with cyclodextrin. The obtained clathrate compound was granulated into powder of 150 mesh or finer with a spray drier at a drying temperature of 60° C. 10 parts by weight of the obtained powder and 90 parts by weight of polyvinyl acetate compound were melt-mixed, and molded into pellets by the underwater cut method. A mixture of 40 parts by weight of the obtained pellets with 60 parts by weight of the polyvinyl acetate compound was molded in the form of film by extrusion molding.

EXAMPLE 5

80 parts by weight of α-cyclodextrin was added to 20 parts by weight of fenitrothion and the mixture was blended under stirring for 1 hour while keeping the temperature at 50° C., to prepare a clathrate compound of fenitrothion with cyclodextrin. The obtained clathrate compound was granulated into powder of 150 mesh or finer with a drum drier at a drying temperature of 60° C. 10 parts by weight of the obtained powder and 90 parts by weight of ethylene-vinyl acetate compound were melt-mixed, and molded into pellets by the sheet cut method. The molded product was further molded in the form of film by extrusion molding.

The insect repelling/killing films obtained by the processes of the above examples all showed not only a homogeneous but prolonged insect repelling/killing effect, because of the appropriate bleeding of the insect repellent/killer contained therein to the surface of the film. The obtained insect repelling/killing film can be applied as follows:

APPLICATION EXAMPLE 1

The present insect repelling/killing film can be used for wrapping fruits to be transported, expecially for prolonged transportation of bananas, oranges, or apples to be imported or exported, so that these fruits can be protected from insect damage during the transportation.

APPLICATION EXAMPLE 2

The present insect repelling/killing film can be used for covering cut flowers or potted plants, on transportation or ornamented, to protect them from insect damage.

APPLICATION EXAMPLE 3

Clothes to be kept for long can be protected from insect damage by wrapping them with the present insect repelling/killing film.

APPLICATION EXAMPLE 4

Tatami or carpets can be protected from mite damage by underlaying the present insect repelling/killing film.

APPLICATION EXAMPLE 5

The present insect repelling/killing film can be used as the lining for bags for packaging cereals, to protect them from so-called insect damage, as the eggs of insects are killed, whereby the storage period can be prolonged.

As described heretofore, the present process for the preparation of insect repelling/killing film, which is characterized in forming a clathrate compound of fenitrothion with cyclodextrin and molding a mixture of said clathrate compound with a synthetic resin material in the form of film, enables molding of films having a homogeneous insect repelling/killing effect because of the homogeneous dispersion of the insect repellent/killer in the film, and also this insect repelling/killing effect is prolonged, because the insect repellent/killer appropriately bleeds to the surface of the film. The strength of the insect repelling/killing ability can be freely selected by varying the amount of fenitrothion or the pellets incorporated in dependence on the types of insects. Moreover, the film having a desired thickness can be molded, including those as thick as plate. Thus the effect of the present insect repelling/killing film is remarkable.

We claim:

1. A process for the preparation of insect repelling/killing film, which comprises forming a clathrate compound of fenitrothion with either cyclodextrin or a starch decomposition product containing cyclodextrin, granulating said clathrate compound into dry powder, melt-mixing said dry powder with a synthetic resin material in a weight ratio ranging from 0.1 to 50%, molding said mixture into pellets, and molding said pellets in the form of a film.

2. A process for the preparation of insect repelling/killing film as set forth in claim 1, wherein said synthetic resin material is an olefin plastic.

3. A process for the preparation of insect repelling/killing film as set forth in claim 1, wherein said synthetic resin material is a soft vinyl chloride plastic.

4. A process for the preparation of insect repelling/killing film as set forth in claim 1, wherein said synthetic resin material is a vinyl acetate plastic.

5. A process for the preparation of insect repelling/killing film as set forth in claim 1, wherein said synthetic resin material has a molding temperature lower than the decomposition temperature of fenitrothion.

6. A process for the preparation of insect repelling/killing film as set forth in claim 1, wherein said synthetic resin material is a polyethylene plastic.

7. A process for the preparation of insect repelling/killing film, which comprises forming a clathrate compound of fenitrothion with either cyclodextrin or a starch decomposition product containing cyclodextrin, granulating said clathrate compound into dry powder, melt-mixing said dry powder with a synthetic resin material in a weight ratio ranging from 0.1 to 50%, molding said mixture into pellets, and molding a mixture of an appropriate amount of said pellets with a synthetic resin material in the form of a film.

8. A process for the preparation of insect repelling/killing film as set forth in claim 7, wherein said synthetic resin material is an olefin plastic.

9. A process for the preparation of insect repelling/killing film as set forth in claim 7, wherein said synthetic resin material is a soft vinyl chloride plastic.

10. A process for the preparation of insect repelling/killing film as set forth in claim 7, wherein said synthetic resin material is a vinyl acetate plastic.

11. A process for the preparation of insect repelling killing film as set forth in claim 7, wherein said synthetic resin material has a molding temperature lower than the decomposition temperature of fenitrothion.

12. A process for the preparation of insect repelling/killing film as set forth in claim 7, wherein said synthetic resin material is a polyethylene plastic.

* * * * *